United States Patent
Akagi

(10) Patent No.: US 11,348,289 B2
(45) Date of Patent: May 31, 2022

(54) MEDICAL IMAGE DISPLAY DEVICE AND MEDICAL IMAGE DISPLAY SYSTEM FOR SUPERIMPOSING ANALYZED IMAGES

(71) Applicant: Konica Minolta, Inc., Tokyo (JP)

(72) Inventor: Eiichi Akagi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 28 days.

(21) Appl. No.: 16/715,196

(22) Filed: Dec. 16, 2019

(65) Prior Publication Data

US 2020/0193651 A1    Jun. 18, 2020

(30) Foreign Application Priority Data

Dec. 14, 2018  (JP) .............................. JP2018-234290

(51) Int. Cl.
*G06T 11/00* (2006.01)
*G06T 7/00* (2017.01)
(Continued)

(52) U.S. Cl.
CPC .......... *G06T 11/001* (2013.01); *G06T 7/0014* (2013.01); *G16H 30/20* (2018.01);
(Continued)

(58) Field of Classification Search
CPC ................. G06T 11/001; G06T 7/0014; G06T 2207/10016; G06T 2207/30068; G06T 2210/41; G16H 30/20; G16H 30/40
See application file for complete search history.

(56) References Cited

U.S. PATENT DOCUMENTS 7,447,346 B2 * 11/2008 Sato .......................... G06T 5/50
382/132
2011/0103663 A1 * 5/2011 Rosenbaum ......... G06K 9/3233
382/131

(Continued)

FOREIGN PATENT DOCUMENTS

JP     H07037056 A      2/1995
JP     2016047294 A  *  4/2016
(Continued)

OTHER PUBLICATIONS

JPO Notice of Reasons for Refusal for corresponding JP Application No. 2018-234290; dated Apr. 19, 2022.

*Primary Examiner* — Terrell M Robinson
(74) *Attorney, Agent, or Firm* — Cantor Colburn LLP

(57) ABSTRACT

A medical image display device includes a hardware processor that (i) acquires an original image and an analyzed image obtained by analyzing the original image from another device, (ii) carries out predetermined image processing on one of the original image and the analyzed image as acquired, or carries out different types of image processing respectively on the original image and the analyzed image, (iii) superimposes the analyzed image as acquired or a processed analyzed image obtained by carrying out image processing on the analyzed image on the original image as acquired or a processed original image obtained by carrying out image processing on the original image to generate a processed superimposed image, and (iv) causes the superimposed image to be displayed on a display.

12 Claims, 3 Drawing Sheets

(51) Int. Cl.
*G16H 30/20* (2018.01)
*G16H 30/40* (2018.01)

(52) U.S. Cl.
CPC ... *G16H 30/40* (2018.01); *G06T 2207/10016* (2013.01); *G06T 2207/30068* (2013.01); *G06T 2210/41* (2013.01)

(56) References Cited

U.S. PATENT DOCUMENTS

| | | | | |
|---|---|---|---|---|
| 2011/0122146 A1* | 5/2011 | Nie | ........................ | G06T 5/004 |
| | | | | 345/589 |
| 2013/0135307 A1* | 5/2013 | Kawasaki | ............... | G06T 15/08 |
| | | | | 345/424 |
| 2013/0272495 A1* | 10/2013 | Bullard | ................ | A61B 6/4233 |
| | | | | 378/37 |
| 2018/0018772 A1* | 1/2018 | Fujiwara | ................. | G06T 11/60 |
| 2018/0197280 A1* | 7/2018 | McLaughlin | ......... | G06T 3/4092 |

FOREIGN PATENT DOCUMENTS

| | | | |
|---|---|---|---|
| JP | 2016047294 A | | 4/2016 |
| JP | 2017018681 A | * | 1/2017 |
| JP | 2017018681 A | | 1/2017 |
| JP | 2018196693 A | | 12/2018 |
| WO | 2013141067 A1 | | 9/2013 |

\* cited by examiner

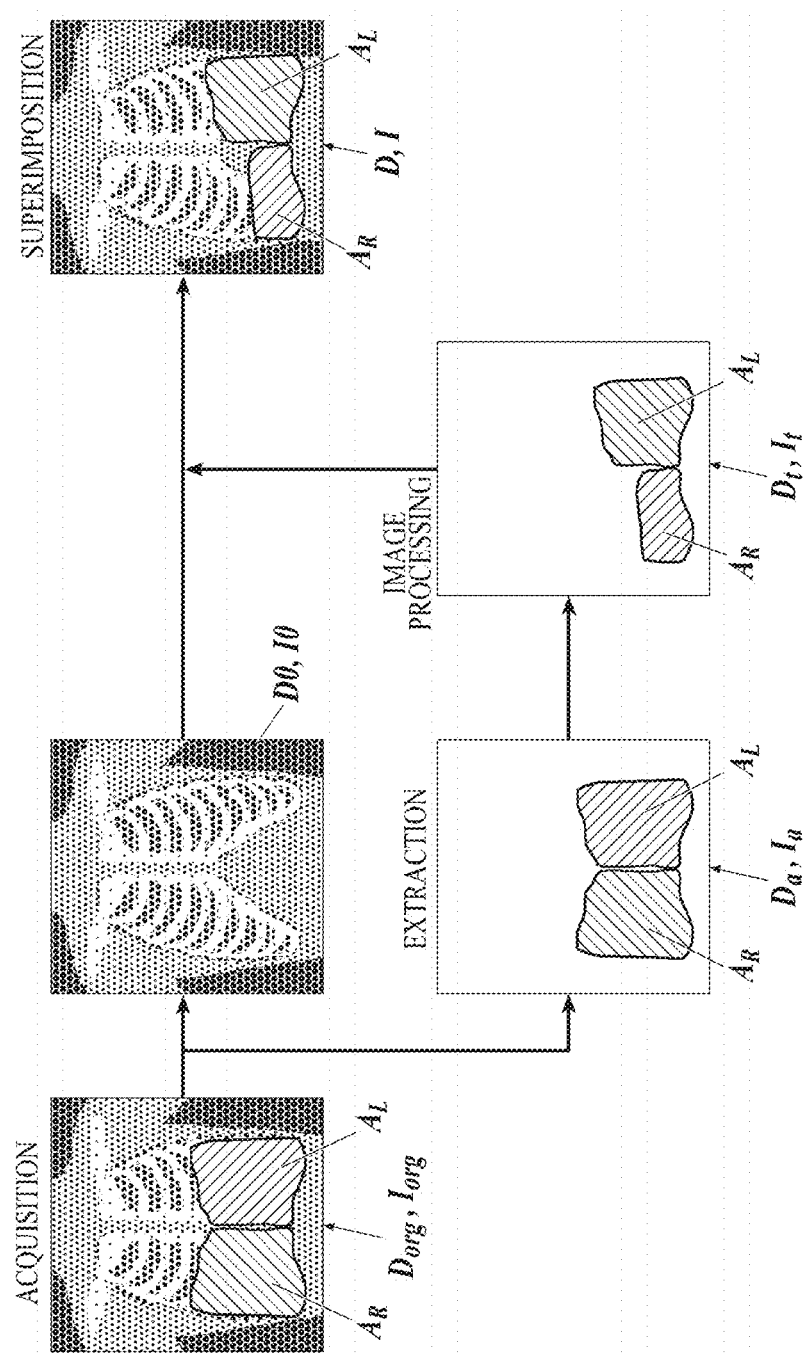

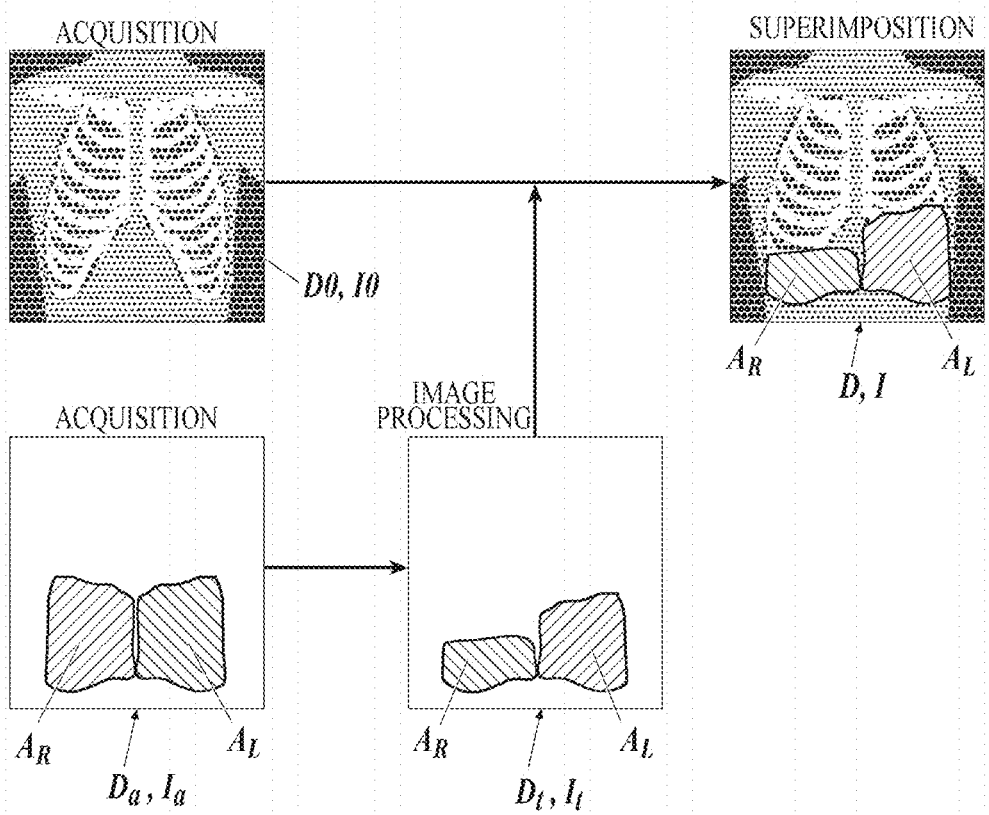

MEDICAL IMAGE DISPLAY DEVICE AND MEDICAL IMAGE DISPLAY SYSTEM FOR SUPERIMPOSING ANALYZED IMAGES

CROSS-REFERENCE TO RELATED APPLICATIONS

The present invention claims priority under 35 U.S.C. § 119 to Japanese Patent Application No. 2018-234290 filed on Dec. 14, 2018, the entire contents of which are incorporated herein by reference.

BACKGROUND

1. Technological Field

The present invention relates to a medical image display device and a medical image display system.

2. Description of the Related Art

A medical image generated in an imaging device is directly displayed on a medical image display device (a PC, mobile terminal, or the like) existing on hand of a doctor, and is used for a diagnosis made by the doctor.

Additional information such as an annotation is conventionally displayed on a medical image in a superimposed manner in a medical image display device. Also under the DICOM standard, graphics, text information, and the like can be displayed in a superimposed manner as a one bit deep overlay by means of the function called Overlay in the group 60xx.

In recent years, a medical image generated in an imaging device may be sent first to an image analysis device, and upon an analysis made by a specialist in charge, sent to a medical image display device together with a result of the analysis, so that the medical image and the result of the analysis are displayed together on the medical image display device to be subjected to a doctor's diagnosis.

On that occasion, a superimposed image obtained by superimposing an analyzed image obtained by analyzing a medical image, for example, instead of graphics or text information, on an original image which is an original medical image is also generated in the image analysis device, and displayed on the medical image display device.

For example, JP2017-018681A describes a dynamic analysis system in which a specific frame (for example, a frame with a maximum point) of a phase matching analysis result image whose transmittance is adjustable is displayed in an overlapping manner on an original analysis result image displayed as video. Accordingly, it is possible to simultaneously check whether or not there is a phase shift in an analysis result in a lung field region and an abnormal portion in terms of blood flow or ventilation without moving eyes.

JP2016-047294A describes a dynamic image analysis device that displays both maps of a ventilation function and a lung blood flow function represented by intensity values or colors in accordance with a feature amount related to the ventilation function and a feature amount related to the lung blood flow function, respectively.

SUMMARY

However, the method currently standardized in DICOM cannot express an overlay having a depth of more than or equal to one bit, and thus, the above-described superimposed image is generated in the form of a superimposed image obtained by embedding an analyzed image in an original image. Therefore, a conventional medical image display device raises an issue that, when attempting to change gradations of an analyzed image in order to make a specific region of the analyzed image easier to view, gradations of the underlying original image also change together, so that it is not possible to monitor both the analyzed image and the original image at the same time with suitable gradations.

On the other hand, many of image analysis devices that analyze medical images are capable of making such a change in gradations for only an analyzed image. However, if a superimposed image is transmitted to an image analysis device and a changed superimposed image is received and displayed each time when the gradations are changed, it is necessary to generate an image in the image analysis device again, which involves an excessive amount of effort and time.

The present invention has an object to enable a doctor to make only an analyzed image easier to view on the spot without taking time when making a diagnosis using a superimposed image obtained by superimposing the analyzed image obtained by analyzing an original image on the original image.

To achieve at least one of the abovementioned objects, according to an aspect of the present invention, a medical image display device includes:

a hardware processor that acquires an original image and an analyzed image obtained by analyzing the original image from another device, carries out predetermined image processing on one of the original image and the analyzed image as acquired, or carries out different types of image processing respectively on the original image and the analyzed image, superimposes the analyzed image as acquired or a processed analyzed image obtained by carrying out image processing on the analyzed image on the original image as acquired or a processed original image obtained by carrying out image processing on the original image to generate a processed superimposed image, and causes the superimposed image to be displayed on a display.

According to another aspect of the present invention, a medical image display system includes:

an imaging device that generates an original image;

an image analysis device that analyzes the original image generated by the imaging device to generate an analyzed image, and outputs the original image and the analyzed image; and a medical image display device including a hardware processor that acquires the original image and the analyzed image obtained by analyzing the original image from the image analysis device, carries out predetermined image processing on one of the original image and the analyzed image as acquired, or carries out different types of image processing respectively on the original image and the analyzed image, superimposes the analyzed image as acquired or a processed analyzed image obtained by carrying out image processing on the analyzed image on the original image as acquired or a processed original image obtained by carrying out image processing on the original image to generate a processed superimposed image, and causes the superimposed image to be displayed on a display.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention.

FIG. 4 is a diagram showing a flow of processing executed by the medical image display device according to the first embodiment.

FIG. 5 is a diagram showing a flow of processing executed by the medical image display device according to the second embodiment.

DETAILED DESCRIPTION OF THE EMBODIMENTS

Figure 1:
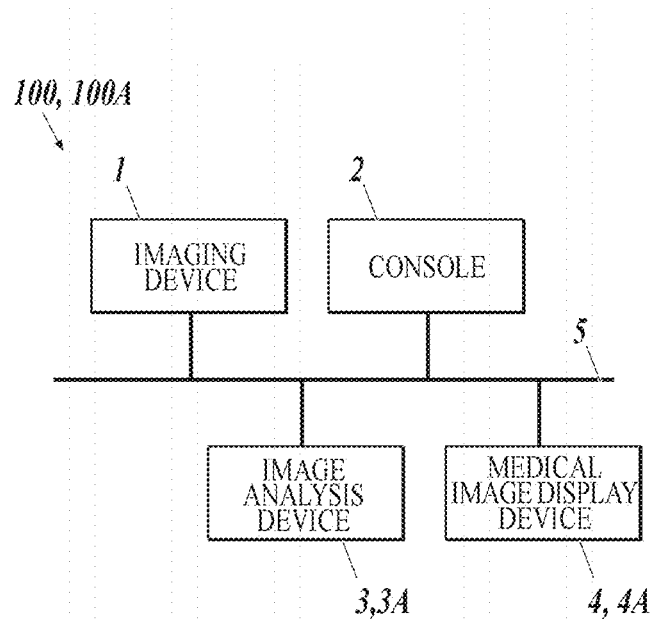
FIG. 1 is a block diagram showing a medical image display system according to a first (second) embodiment of the present invention.

Hereinafter, one or more embodiments of the present invention will be described with reference to the drawings. However, the scope of the invention is not limited to the disclosed embodiments.

First Embodiment

A first embodiment of the present invention will be described with reference to FIG. 1 to FIG. 4.

Note that reference characters in parentheses in FIG. 1 to FIG. 3 will be described later in a second embodiment.

Radiography System

A schematic configuration of a medical image display system 100 according to the embodiment will be described first. FIG. 1 is a block diagram showing the medical image display system 100.

The medical image display system 100 of the embodiment includes an imaging device 1, a console 2, an image analysis device 3, and a medical image display device 4 as shown in FIG. 1.

They communicate with each other via a communication network 5.

The medical image display system 100 is capable of connecting to a hospital information system (HIS), a radiology information system (RIS), a picture archiving and communication system (PACS), and the like, neither shown.

The imaging device 1 only has to be capable of generating a medical image to be analyzed by the image analysis device 3 which will be described later, and a radiographic image capturing device that generates a radiographic image in accordance with radiation produced by a radiation production device, for example, or the like can be used.

Note that the imaging device may be connected to the communication network 5 via the console 2, the image analysis device 3, or the like, instead of being directly connected to the communication network 5.

A medical image may be transmitted from the imaging device 1 to another device 2 or 3 using a storage medium or a cable, instead of being transmitted via the communication network 5.

The console 2 is composed of a PC or dedicated device.

The console 2 enables various imaging conditions (a tube voltage, a tube current, an irradiation time (mAs value), a frame rate, and the like) to be set for an imaging device or the like on the basis of examination information acquired from another device or the like (such as HIS or RIS) or an operation made by an operator.

The image analysis device 3 is composed of a PC, dedicated device, virtual server on a cloud, or the like.

The image analysis device 3 is capable of analyzing a medical image acquired from an imaging device to generate an analyzed image, and outputting the medical image and the analyzed image.

Hereinafter, a medical image to be a source of an analyzed image will be referred to as an "original image I0".

Details of this image analysis device 3 will be described later.

The medical image display device 4 in the embodiment is composed of a PC, mobile terminal, dedicated device, or the like.

Details of this medical image display device 4 will also be described later.

Image Analysis Device

A specific configuration of the image analysis device 3 that the above-described medical image display system 100 includes will be described. FIG. 2 is a block diagram showing the image analysis device 3.

Figure 2:
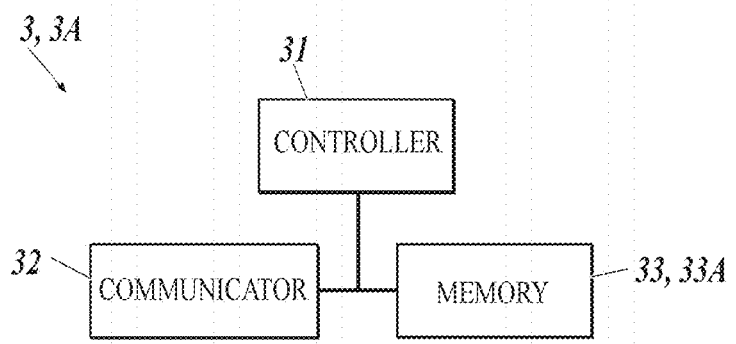
FIG. 2 is a block diagram showing an image analysis device that the medical image display system shown in FIG. 1 includes.

The image analysis device 3 according to the embodiment includes a controller 31 (hardware processor), a communicator 32, and a memory 33 as shown in FIG. 2.

The controller 31 is composed of a CPU (central processing unit), RAM (random access memory), and the like. The CPU of the controller 31 reads out various programs held in the memory 33 for expansion into the RAM, and executes various types of processing in accordance with the expanded programs to exert centralized control over the respective components of the image analysis device 3.

The communicator 32 is composed of a wireless module or the like, and is capable of transmitting/receiving various signals and various types of data to/from other devices 1, 2, 4, and the like connected via the communication network 5 (LAN (local area network), WAN (wide area network), the Internet, or the like).

The memory 33 is composed of a nonvolatile semiconductor memory, hard disk, or the like, and holds various programs to be executed by the controller 31, parameters necessary for execution of the programs, and the like.

The memory 33 is capable of holding various images (an original image and an analyzed image).

The controller 31 of the image analysis device 3 configured in this manner has the following functions.

For example, the controller 31 has a function of acquiring data about an original image from another device or the like (the imaging device 1, the console 2, or the like) via the communicator 32.

A still image and a dynamic image having a plurality of frame images are included in the original image acquired here.

The controller 31 has a function of analyzing the acquired original image, and generating an analyzed image.

Specifically, the controller 31 performs at least any of various types of processing such as specific component differentiating processing, specific component tracking processing, specific signal changing amount extraction processing, specific similar waveform pattern extraction processing, and integrated image differentiating processing.

Among them, the "specific component differentiating processing" is processing of reducing a signal value of a specific region (for example, a rib or clavicle in a lung field) in an imaging target area to increase visibility of a region other than the specific region.

The "specific component tracking processing" is processing of calculating the amount of movement and speed of a specific region (for example, the diaphragm) in an imaging target area and calculating the distance between two different specific regions (for example, between the apex of a lung and the diaphragm).

The "specific signal changing amount extraction processing" is processing of visualizing the amount of changes in signal value by the color difference.

The "specific similar waveform pattern extraction processing" is processing of visualizing the similarity to a specific signal change by the color difference.

The "integrated image differentiating processing" is processing of visualizing the total amount of signal changes during imaging by displaying a difference between an integrated image with a maximum signal value and an integrated image with a minimum signal value.

Note that some of these analyses can also be performed in combination.

The controller 31 has the function of transmitting data about the analyzed image to the medical image display device 4 via the communicator 32.

The original image and the analyzed image are output in the form of data about a superimposed image Iorg (hereinafter, the superimposed image data Dorg (see FIG. 4)) obtained by integrating the analyzed image into the original image.

Medical Image Display Device

A specific configuration of the medical image display device 4 that the above-described medical image display system includes will be described. FIG. 3 is a block diagram showing the medical image display device 4, and FIG. 4 is a diagram showing a flow of processing executed by the medical image display device 4.

Figure 3:
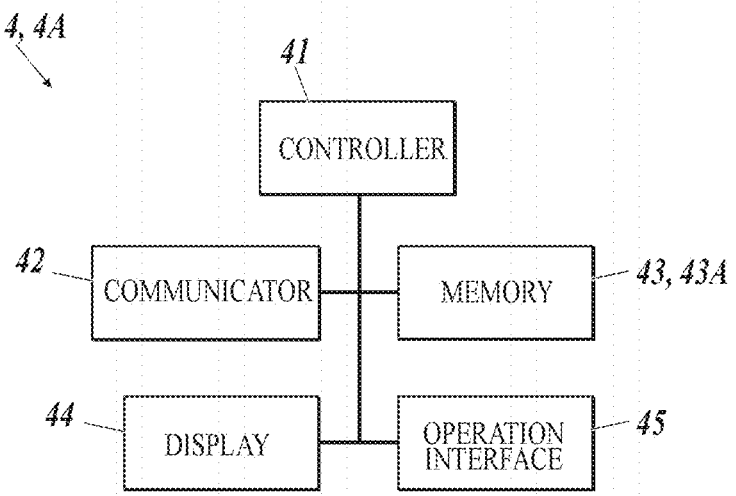
FIG. 3 is a block diagram showing a medical image display device that the medical image display system shown in FIG. 1 includes.

The medical image display device 4 according to the embodiment includes a controller 41, a communicator 42, a memory 43, a display 44, and an operation interface 45 as shown in FIG. 3.

The controller 41 and the communicator 42 are configured similarly to the controller 31 and the communicator 32 in the image analysis device 3.

The memory 43 is composed of a nonvolatile semiconductor memory, hard disk, or the like, and holds various programs to be executed by the controller 41, parameters necessary for execution of the programs, and the like.

The memory 43 is capable of holding data about the original image I0 (hereinafter, original image data D0) acquired from the imaging device 1, data about the analyzed image Ia (hereinafter, analyzed image data Da) generated by the image analysis device 3, data about a processed original image obtained by performing image processing by itself, data about a processed analyzed image It (hereinafter, processed analyzed image data Dt), and data about a processed superimposed image I (hereinafter, processed superimposed image data D).

Note that a plurality of different numeric values to be parameters for gradation processing which will be described later may be stored in the memory 43 as presets.

The display 44 is composed of a monitor such as a LCD (liquid crystal display) or CRT (cathode ray tube), and displays various images, various types of information, and the like in accordance with an instruction of a display signal input from the controller 41.

The operation interface 45 is composed of a keyboard including a cursor key, number input keys, various functional keys, and the like, a pointing device such as a mouse, a touch panel laminated on the surface of the display 44, and the like so as to allow an operator to operate.

The operation interface 45 outputs various signals based on operations performed by the operator to the controller 31.

Note that an operation interface may be provided for the console 2, the image analysis device 3, or the like, instead of providing the operation interface 45 for the medical image display device 4.

The controller 41 of the medical image display device 4 configured in this manner has the following functions.

For example, the controller 41 has the function of acquiring the original image I0 and the analyzed image Ia obtained by analyzing the original image I0 from another device.

Since the image analysis device 3 outputs the original image and the analyzed image in the form of the superimposed image data Dorg obtained by integrating the analyzed image Ia into the original image I0 in the embodiment as described above, the controller 41 according to the embodiment acquires the original image I0 and the analyzed image Ia as shown in FIG. 4, for example, in the form of the superimposed image data Dorg.

The controller 41 according to the embodiment has the function of extracting the analyzed image Ia from the superimposed image data Dorg.

For example, in a case where the original image I0 is a radio fluoroscopy (RF) image, and the analyzed image Ia of the original image I0 is presented in blue, a signal value of each pixel in the analyzed image Ia before being subjected to the gradation processing which will be described later is calculated using Equations (1-1) to (1-3) below because the original image I0 and the analyzed image Ia are monochrome images.

$$Ra0=0 \tag{1-1}$$

$$Ga0=0 \tag{1-2}$$

$$Ba0=Borg-Rorg \tag{1-3}$$

Here, $Ra0$ represents a red component of the analyzed image Ia, $Ga0$ represents a green component of the analyzed image Ia, $Ba0$ represents a blue component of the analyzed image Ia, $Rorg$ represents a red component of the superimposed image Iorg, and $Borg$ represents a blue component of the superimposed image Iorg.

A signal value of each pixel in the original image I0 can be calculated using Equations (2-1) to (2-3) below.

$$R0=Rorg \tag{2-1}$$

$$G0=Gorg \tag{2-2}$$

$$B0=Borg-Ba \tag{2-3}$$

Here, $R0$ represents a red component of the original image I0, $G0$ represents a green component of the original image I0, $B0$ represents a blue component of the original image I0, $Rorg$ represents a red component of the superimposed image Iorg, $Gorg$ represents a green component of the superimposed image Iorg, and $Borg$ represents a blue component of the superimposed image Iorg.

By performing these calculations, the superimposed image data Dorg is separated into the original image data D0 and the analyzed image data Da as shown in FIG. 4.

The controller 41 according to the embodiment has a function of:

carrying out predetermined image processing on one of the analyzed image Ia as extracted and the original image I0 left after the analyzed image Ia is extracted; or carrying out different types of image processing on both the original image I0 and the analyzed image Ia, respectively.

In the embodiment, at least any of gradation processing, transmittance changing processing, hue changing processing, persistence-of-vision image generation processing, frequency enhancement processing, outline extraction processing is carried out as image processing.

For example, in a case of carrying out the gradation processing as image processing, the controller 41 first accepts settings of various parameters to be used when performing the processing. When a user sets parameters via the operation interface 45 or the like, the controller 41 calculates a signal value of each pixel in a processed analyzed image using Equation (3) below, for example.

$$Sa = l \times Sa0 + m \quad (3)$$

Sa0 represents each of red, green, and blue signal values (Ra0, Ga0, Ba0) of the analyzed image Ia. Sa represents each of red, green, and blue signal values (Ra, Ga, Ba) of the processed analyzed image It. l represents an inclination. m represents an offset.

When setting is made such that l=2.0 and m=0, for example, changes in signal value are enhanced, so that small changes are easily recognized.

Note that, in a case of carrying out the gradation processing on both the original image I0 and the analyzed image Ia, parameters to be applied respectively are made different in value.

By storing a plurality of such combinations of the value of l and the value of m in the memory 43 as presets, and associating each of the presets with the operation interface 45, a corresponding preset may be acquired from the memory 43 on the basis of an operation on the operation interface 45 performed by a user, and the gradation processing may be performed on the basis of the acquired preset.

The transmittance changing processing is processing of changing transmittance.

In a case of carrying out this transmittance changing processing, the controller 41 first accepts a setting of transmittance α (%) of an image targeted for processing. When a user sets the transmittance α via the operation interface 45 or the like, the controller 41 calculates a signal value of each pixel in the superimposed image Iorg using Equation (4) below, for example.

$$S = Sa \times \alpha/100 + Sorg \times (1 - \alpha/100) \quad (4)$$

S represents each of red, green, and blue signal values of the superimposed image Iorg. Sa represents each of red, green, and blue signal values of the processed analyzed image It. α represents transmittance.

Note that, in a case of carrying out the transmittance changing processing on both the original image I0 and the analyzed image Ia, values of the transmittance α set respectively are made different.

The hue changing processing is processing of changing the hue when making display.

In a case of carrying out the hue changing processing, the controller 41 first accepts a hue setting. When a user sets a hue via the operation interface 45 or the like, the controller 41 adjusts a signal value of a target image so as to obtain the set hue.

Note that, in a case of carrying out the hue changing processing on both the original image I0 and the analyzed image Ia, hues set respectively are made different.

In a case where a medical image targeted for the hue changing processing is a breast dynamic image, the hue during an expiratory action and the hue during an inspiratory action may be made different from each other. Such a configuration is effective for making a dynamic image easier to view because display of a dynamic image (in particular, an analyzed dynamic image having been subjected to a dynamic analysis, or the like) changes over time to become more difficult to view than a still image.

The persistence-of-vision image generation processing is processing of reflecting, on a signal value of each pixel, specific signal values during a past predetermined time duration of each pixel to generate a persistence-of-vision image.

A maximum value and minimum value of a signal value, a maximum value and minimum value of a corrected signal value obtained by subjecting the signal value to predetermined correction, and the like are included in the specific signal values.

In a case of carrying out the persistence-of-vision image generation processing, the controller 41 refers to signal values of a pixel at an identical position in a plurality of frames in a past predetermined period in a dynamic image targeted for processing, and employs the maximum or minimum signal value among them as the signal value of the pixel. Alternatively, for a signal value of a pixel at an identical position in a plurality of frames in a past predetermined period, the maximum signal value among values obtained by subtracting a signal value in accordance with the magnitude of a time difference between a past frame and a current frame may be used.

The frequency enhancement processing is processing of enhancing the frequency of an edge portion in a specific region of an image to sharpen the specific region.

The outline extraction processing is processing of converting an image targeted for processing into an image in which only the outline of a subject appears.

By performing these calculations, the processed analyzed image data Dt is generated from the analyzed image data Da, and processed original image data is generated from the original image data D0, as shown in FIG. 4.

The controller 41 has the function of superimposing the analyzed image Ia as extracted or a processed analyzed image obtained by carrying out image processing on the analyzed image Ia on the original image I0 left after the analyzed image Ia is extracted or a processed original image obtained by carrying out image processing on the original image I0 to generate a processed superimposed image I.

In the embodiment, a signal value of each pixel in the processed superimposed image I is calculated using Equation (5) below, for example.

$$S = Sa + \alpha \times S0 \quad (5)$$

S represents each of red, green, and blue signal values of the processed superimposed image I. α represents a blending coefficient. S0 represents each of red, green, and blue signal values of the original image I0.

By performing this calculation, the processed superimposed image I obtained by superimposing the processed analyzed image It on the original image I0 is generated, the processed superimposed image I obtained by superimposing the analyzed image Ia on the processed original image is generated, and the processed superimposed image I obtained by superimposing the processed analyzed image It on the processed original image is generated, as shown in FIG. 4.

The controller 41 has the function of causing the processed superimposed image I as generated to be displayed on the display 44.

For example, in a case of carrying out the gradation processing on the analyzed image Ia before generating the processed superimposed image I, there is no difference seen between analysis results AR and AL of the left and right lung fields in the analyzed image Ia analyzed with an initial parameter immediately after being acquired from the image analysis device 3 as shown in FIG. 4, for example. By reducing a threshold value about whether or not a display is made through the gradation processing, a superimposed image in the stage displayed on the medical image display device 4 can be displayed in such a manner that the analysis results AR and AL (ranges to be displayed) of the left and right lung fields are distinguished. FIG. 4 illustrates a case in which the display range of the analysis result of the right lung is narrower. This enables a diagnosis to be made in more detail.

When displaying a rib attenuated image generated by carrying out the specific component differentiating processing, for example, on the original image I0 in an overlapping manner, a superimposed image in which the original image I0 is seen through the rib attenuated image can be displayed by carrying out the transmittance changing processing as image processing.

Although the specific configuration of the medical image display device 4 according to the embodiment has been described above, at least some of the above-described various functions that the medical image display device 4 has may be provided for the console 2, another device having a display, or the like.

As described above, in accordance with the medical image display system 100 according to the embodiment, the image quality of one of the original image I0 and the analyzed image Ia in a superimposed image obtained by superimposing the analyzed image Ia on the original image I0 is changed with respect to the image quality of the other one, so that the analyzed image Ia can be made relatively easier to view.

The medical image display device 4 is composed of a PC, mobile terminal, or the like, and thus can be arranged at a place where a doctor makes a diagnosis, and the doctor himself/herself can carry out image processing on at least one of the original image I0 and the analyzed image Ia without forwarding the original image I0 and the analyzed image Ia to the image analysis device 3. Therefore, the doctor can make only the analyzed image Ia easier to view on the spot without taking time.

Second Embodiment

A second embodiment of the present invention will be described with reference to FIG. 1 to FIG. 3 and FIG. 5. Note that components similar to those of the above-described first embodiment will be provided with the same reference characters, and their description will be omitted.

A medical image display system 100A (see FIG. 1) according to the embodiment is different from the medical image display system 100 according to the above-described first embodiment in terms of the data format of the original image I0 and the analyzed image Ia forwarded from an image analysis device 3A (see FIG. 1 and FIG. 3) to the medical image display device 4 (see FIG. 1 and FIG. 3).

Specifically, the image analysis device 3A according to the embodiment is different from the image analysis device 3 of the above-described first embodiment in terms of programs held in a memory 33A.

Accordingly, the controller 31 of the image analysis device 3A according to the embodiment outputs the original image I0 and the analyzed image Ia in the form of separate independent pieces of data (the original image data D0 and the analyzed image data Da), while the image analysis device 3 of the above-described first embodiment outputs the original image I0 and the analyzed image Ia in the form of the superimposed image Iorg (the superimposed image data Dorg) obtained by superimposing the analyzed image Ia on the original image I0.

Note that specific details of analysis are similar to those of the above-described first embodiment.

The medical image display device 4A according to the embodiment is different from the medical image display device 4 of the above-described first embodiment in terms of programs held in a memory 43A.

Accordingly, the controller 41 of the medical image display device 4A according to the embodiment acquires the original image I0 and the analyzed image Ia in the form of separate independent pieces of data D0 and Da as shown in FIG. 5, for example, while the medical image display device 4 of the above-described first embodiment acquires the original image I0 and the analyzed image Ia in the form of the superimposed image Iorg obtained by superimposing the analyzed image Ia on the original image I0.

Therefore, the medical image display device 4A according to the embodiment does not have the function of extracting an analyzed image from integrated data that the medical image display device 4 of the above-described first embodiment has.

The controller 41 has a function of:

carrying out predetermined image processing on one of the original image I0 and the analyzed image Ia as acquired; or carrying out different types of image processing on both the original image I0 and the analyzed image Ia, respectively.

Note that details of specific image processing are the same as those of the above-described first embodiment.

The controller 41 has a function of superimposing the analyzed image Ia as acquired or the processed analyzed image It obtained by carrying out image processing on the analyzed image Ia on the original image I0 as acquired or a processed original image obtained by carrying out image processing on the original image I0 to generate the processed superimposed image I.

Note that a specific method of generating the processed superimposed image I is the same as that of the above-described first embodiment.

As described above, in accordance with the medical image display system 100A according to the embodiment, the image quality of one of the original image I0 and the analyzed image Ia in the superimposed image Iorg obtained by superimposing the analyzed image Ia on the original image I0 is changed with respect to the image quality of the other one, so that the analyzed image Ia can be made relatively easier to view, similarly to the medical image display system 100 of the above-described first embodiment.

The medical image display device 4A is composed of a PC, mobile terminal, or the like, and thus can be arranged at a place where a doctor makes a diagnosis, and the doctor himself/herself can carry out image processing on at least one of the original image I0 and the analyzed image Ia without forwarding the original image I0 and the analyzed image Ia to the image analysis device 3A. Therefore, the doctor can make only the analyzed image Ia easier to view on the spot without taking time.

Although embodiments of the present invention have been described and illustrated in detail, the disclosed embodiments are made for purposes of illustration and example only and not limitation. The scope of the present invention should be interpreted by terms of the appended claims.

What is claimed is:

1. A medical image display device, comprising:
a hardware processor that
acquires an original image and an analyzed image in a form of integrated data obtained by superimposing the analyzed image onto the original image from another device,
separates integrated data into the original image and the analyzed image,
carries out predetermined image processing on one of the original image and the analyzed image as acquired, or carries out different types of image processing respectively on the original image and the analyzed image,
superimposes:
a processed analyzed image obtained by carrying out image processing on the analyzed image onto the original image as acquired;
the analyzed image as acquired onto a processed original image obtained by carrying out image processing on the original image; or
the processed analyzed image obtained by carrying out the image processing on the analyzed image onto the processed original image obtained by carrying out the image processing on the original image to generate a processed superimposed image, and
causes the superimposed image to be displayed on a display.

2. The medical image display device according to claim 1, wherein the hardware processor
carries out image processing on at least one of the analyzed image extracted from the integrated data and the original image left after the analyzed image is extracted, and
superimposes one of:
the analyzed image as extracted; or
a processed analyzed image obtained by carrying out image processing on the analyzed image on the original image left after the analyzed image is extracted; or
a processed original image obtained by carrying out image processing;
on the original image to generate a processed superimposed image.

3. The medical image display device according to claim 1, wherein the hardware processor
acquires the original image and the analyzed image in a form of independent pieces of data, respectively,
carries out image processing on at least one of the analyzed image and the original image as acquired, and
superimposes one of:
the analyzed image as acquired; or
a processed analyzed image obtained by carrying out image processing on the analyzed image on the original image as acquired; or
a processed original image obtained by carrying out image processing;
on the original image to generate a processed superimposed image.

4. The medical image display device according to claim 1, wherein the hardware processor carries out gradation processing as the image processing.

5. The medical image display device according to claim 4, further comprising:
an operation interface that can be operated by a user; and
a memory that stores different numeric values to be parameters for the gradation processing as presets,
wherein the hardware processor acquires a corresponding preset from the memory on a basis of an operation that the user has performed on the operation interface, and performs the gradation processing based on the acquired preset.

6. The medical image display device according to claim 1, wherein the hardware processor carries out transmittance changing processing of changing transmittance as the image processing.

7. The medical image display device according to claim 1, wherein the hardware processor carries out hue changing processing of changing a hue when making a display as the image processing.

8. The medical image display device according to claim 1, wherein the original image is a dynamic image having a plurality of frame images.

9. The medical image display device according to claim 8, wherein the hardware processor carries out, as the image processing, persistence-of-vision image generation processing of reflecting a specific signal value of each pixel in a past predetermined period on a signal value of each pixel to generate a persistence-of-vision image.

10. The medical image display device according to claim 9, wherein the hardware processor carries out frequency enhancement processing or outline extraction processing as the image processing.

11. The medical image display device according to claim 8, wherein, in a case where an analyzed image targeted for processing is a breast dynamic image, the hardware processor carries out, as the image processing, hue changing processing of making a hue during an expiratory action and a hue during an inspiratory action different from each other.

12. A medical image display system, comprising:
an imaging device that generates an original image;
an image analysis device that analyzes the original image generated by the imaging device to generate an analyzed image, and outputs the original image and the analyzed image; and
a medical image display device including a hardware processor that
acquires the original image and the analyzed image in a form of integrated data obtained by superimposing the analyzed image onto the original image from the image analysis device,
separates integrated data into the original image and the analyzed image,
carries out predetermined image processing on one of the original image and the analyzed image as acquired, or carries out different types of image processing respectively on the original image and the analyzed image,
superimposes:
a processed analyzed image obtained by carrying out image processing on the analyzed image onto the original image as acquired;
the analyzed image as acquired onto a processed original image obtained by carrying out image processing on the original image; or the processed analyzed image obtained by carrying out the image processing on the analyzed image onto the processed original image obtained by carrying out the image processing on the original image to generate a processed superimposed image, and
causes the superimposed image to be displayed on a display.

\* \* \* \* \*